United States Patent
Sokal et al.

[11] Patent Number: 5,819,742
[45] Date of Patent: Oct. 13, 1998

[54] VAGINAL DEVICE FOR PREVENTING CONCEPTION OR THE TRANSMISSION OF SEXUALLY TRANSMITTED DISEASES, OR BOTH

[75] Inventors: David C. Sokal, Mebane; Laneta J. Dorflinger, Durham, both of N.C.; J.V. Tapani Luukkainen, Espoo, Finland; Parthena M. Martin, Chapel Hill, N.C.

[73] Assignee: Family Health International, Durham, N.C.

[21] Appl. No.: 960,898

[22] Filed: Oct. 30, 1997

Related U.S. Application Data

[60] Provisional application No. 60/030,361 Nov. 6, 1996.
[51] Int. Cl.⁶ ....................................................... A61F 6/06
[52] U.S. Cl. ............................................. 128/830; 128/832
[58] Field of Search ..................................... 128/830–841

[56] References Cited

U.S. PATENT DOCUMENTS

| | | |
|---|---|---|
| 3,398,737 | 8/1968 | Sheppard et al. . |
| 3,763,861 | 10/1973 | Forti et al. . |
| 3,780,730 | 12/1973 | Weisman ................................. 128/832 |
| 3,916,898 | 11/1975 | Robinson . |
| 3,923,939 | 12/1975 | Baker et al. . |
| 4,186,742 | 2/1980 | Donald . |
| 4,286,593 | 9/1981 | Place et al. . |
| 4,360,013 | 11/1982 | Barrows ................................. 128/832 |
| 4,369,773 | 1/1983 | Chvapil . |
| 4,564,362 | 1/1986 | Burnhill . |
| 4,589,880 | 5/1986 | Dunn et al. . |
| 4,601,714 | 7/1986 | Burnhill . |
| 4,631,060 | 12/1986 | Place . |
| 4,788,060 | 11/1988 | Endicott ................................... 604/36 |
| 4,848,572 | 7/1989 | Herrera ................................... 604/358 |
| 5,201,326 | 4/1993 | Kubicki ................................... 128/832 |
| 5,231,992 | 8/1993 | Leon . |

*Primary Examiner*—Michael A. Brown
*Attorney, Agent, or Firm*—Richard S. Faust

[57] ABSTRACT

A vaginal device provides physical and chemical barriers to contraception or protection against sexually transmitted diseases, or both. The device includes a towelette having approximately 5 ml of preventive formulation incorporated therein by absorption. During intercourse, the towelette rests in the upper vagina and effectively functions as both a physical and chemical barrier to contraception. In some embodiments, the towelette may become compressed into a crumpled, disc-like shape, which may enhance its properties as a physical barrier. Means to facilitate insertion and removal of the device are described.

20 Claims, 6 Drawing Sheets

VAGINAL DEVICE FOR PREVENTING CONCEPTION OR THE TRANSMISSION OF SEXUALLY TRANSMITTED DISEASES, OR BOTH

CROSS REFERENCE TO RELATED APPLICATION

This application claims the benefit under Title 35, United States Code §119(e) of U.S. Provisional patent application Ser. No. 60/030,361, filed Nov. 6, 1996.

FIELD OF THE INVENTION

The invention relates to a vaginal device providing physical and chemical barriers to contraception or protection against sexually transmitted diseases (STDs), or both.

BACKGROUND OF THE INVENTION

Vaginal sponge contraceptives have gained favor as a single-use contraceptive providing a physical barrier to sperm entry to the cervical canal as well as a chemical barrier due to a chemical spermicidal agent typically included in the sponge. Vaginal sponges are formed of compressible polyurethane foam or other plastic foam material in the shape of a sphere, disc or doughnut. The sponge, when inserted into the vagina to cover the cervical area, has the ability to absorb sperm and block passage of sperm to the cervical canal. Additionally, spermicide may be released from the sponge to create the mentioned simultaneous chemical barrier. Disadvantages of the sponge include its expense and its large size and resultant bulky packaging requirements. Also, in its usual application, the sponge does not provide material protection against transmission of STDs.

The well-known diaphragm method of female vaginal contraception provides a physical barrier to passage of sperm to the cervical canal. The diaphragm is also used in association with spermicides. A major disadvantage of the diaphragm is the need for careful and accurate placement of the device so that it properly covers the cervix. In addition, because of the nature of diaphragms, they are unable to retain spermicidal agents except in the concave side of the "dome" diaphragm.

While the sponge and diaphragm, as well as other physical barrier female contraceptive devices such as the cervical cap, provide relatively reliable blockage of sperm to the cervical canal, and these devices may be used with spermicides, there is a need for a reliable, highly effective, low cost barrier contraceptive method that addresses the above mentioned disadvantages of the sponge and diaphragm while providing protection against both pregnancy and STDs.

SUMMARY OF THE INVENTION

In one basic aspect, the present invention may be defined as a vaginal device providing physical and chemical barriers to contraception, or protection against sexually transmitted diseases, or both. The device includes a towelette formed of absorbent sheet material sized to fit within the vagina of a human female while permitting intercourse to take place, and a flowable preventive formulation incorporated into the towelette by absorption. As used herein, the term "preventive formulation" designates the active chemical agents that may be used with this device. The preventive formulation may include one or more pharmacologically active agents. The preventive formulation may also include other additives well known to those in the pharmaceutical industry, whose purpose may be to aid in the preservation of the active agents, or to improve the functionality or acceptability of the product. The preventive formulation may have the following functions:

1. prevention of conception (contraception);
2. prevention of the transmission of sexually transmitted diseases; or
3. both of the above.

The vaginal device may be provided with means, hand-engagable by a female user, for facilitating removal of the device. The removal means may take the form of a hand-engagable structure at the peripheral edges of the towelette, a string, or a ring that is inserted with the device. Preferably, the towelette sheet material is a nonwoven fabric that has the ability to carry approximately 5 ml of gel. Preferred materials include polyester and polyester/cotton blends. Such fabrics may permit printing of instructions for use on the device itself.

In another aspect, the invention may be defined as a method for providing contraception comprising insertion of a vaginal device as described above into the vagina of a human female prior to intercourse and permitting the towelette of the device to become compressed into a crumpled disc-like shape in the upper vagina during intercourse where the towelette effectively functions in both physical and chemical barrier modes.

BRIEF DESCRIPTION OF THE DRAWINGS

Some of the objects having been stated, other objects will appear as the description proceeds, when taken in connection with the accompanying drawings, in which

FIG. 13 is a pictorial view of a unitary vaginal device having a flexible ring joined to appropriate sheet material to define a dome and depending skirt. While FIG. 13 shows a depending skirt, which is large in relation to the ring, the depending skirt may be quite small, e.g. extending only 1 cm beyond the ring.

DETAILED DESCRIPTION OF THE INVENTION

While the present invention will be described more fully hereinafter with reference to the accompanying drawings, in which aspects of the preferred manner of practicing the present invention are shown, it is to be understood at the outset of the description which follows that persons of skill in the appropriate arts may modify the invention herein described while still achieving the favorable results of this invention. Accordingly, the description which follows is to be understood as being a broad, teaching disclosure directed to persons of skill in the appropriate arts, and not as limiting upon the present invention.

Figure 1:
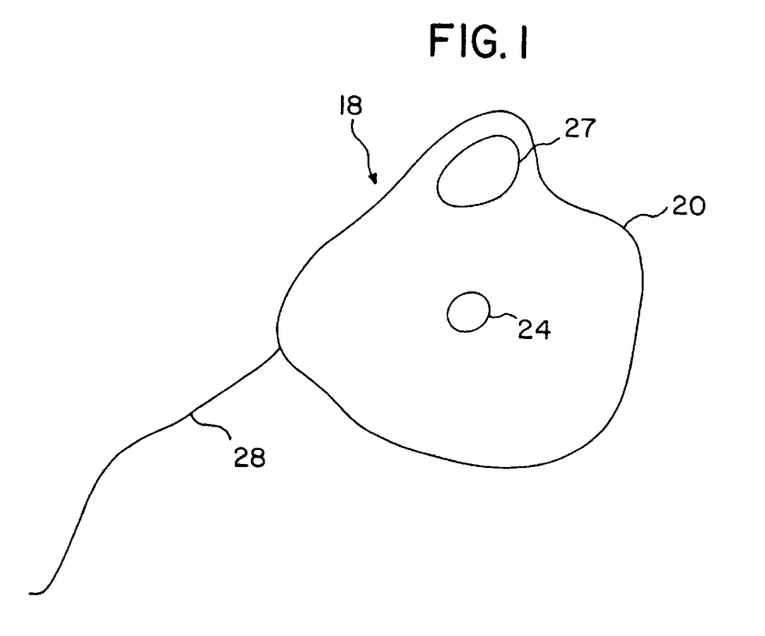
FIG. 1 is a top view of a vaginal device of the invention including a towelette containing a preventive formulation.

Referring to the drawings and particularly to FIG. 1, there is shown a first embodiment of a vaginal device 18 of the present invention. Device 18 includes a towelette 20 that takes the form of a piece of absorbent, crushable, tear resistant sheet material which may be similar to the sheet material forming commonly used hand wipes or baby wipes. More particularly, the towelette may be made of a nonwoven fabric. The fabric should contain no loose fibers and should be strong (able to withstand an 8—10 lb. force before failure in either direction). The material should have the appropriate properties of absorbency, penetration, and retention to carry 5 milliliters of gel. Preferably, the material is biodegradable or disposable by burning. Preferred materials include polyester, or polyester/cotton blends. An advantage of using polyester is the possibility of using thermal bonding. Many of the materials suitable for towelettes of the present invention are well known to those skilled in the art. The towelette can be made from many of the same materials which are suitable for use as a moist wipe, including meltblown, coform, air-laid, bonded-carded web materials, hydroentangled materials and the like and can comprise synthetic or natural fibers or combinations thereof. The towelette may have a basis weight of from about 25 to about 120 grams per square meter and desirably from about 40 to about 90 grams per square meter.

Towelette 20 may have any desired shape such as square, rectangular, oval or circular, with either smooth or scalloped edges. When laid flat, the surface area of towelette 20 may range from approximately 9 to 36 square inches. This total area has been found suitable for the towelette to carry an effective amount of preventive formulation, and for the towelette to be crushed into a round disc-like shape during intercourse.

Towelette 20 is moistened with a flowable preventive formulation that may be liquid, cream or gel, and which may also have lubricating and/or foaming qualities. In certain embodiments, the foaming property of a chemical agent such as hydrogen peroxide (that may be located between the folds or between two thicknesses of the towelette) may be used to cause the towelette, during intercourse, to cause the towelette, after insertion into the vagina, to increase in volume and to become a more effective physical barrier. A foaming agent such as hydrogen peroxide may also be used to enhance diffusion of the preventive formulation within the vagina.

Figure 4:
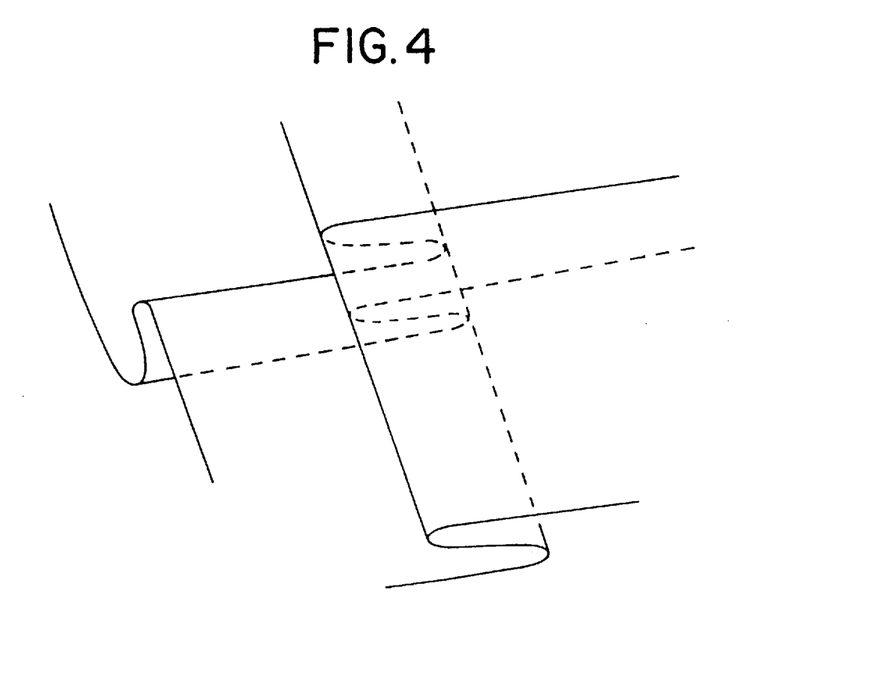
FIG. 4 is an enlarged detailed view of a portion of a towelette showing the folds made in the manufacturing process to provide reservoir-like spaces for holding an amount of protective formulation beyond that which can be absorbed into the towelette material.

Towelette 20 includes an optional spermicide reservoir 24 located approximately in the middle of the towelette so that a larger volume of the preventive formulation may be delivered into the vagina than is absorbed by the towelette itself. Reservoir 24 may consist of a separately formed volume as shown in FIG. 1. A reservoir may also be formed by a space between layers of the towelette created by folding the towelette (FIG. 4), or simply by the space between the folds of the wipe, without any special folding or other provisions for the spermicide.

A removal means in the form of a length of string 28 is attached to towelette 20 so that the towelette can be easily removed after intercourse. A supplemental removal means in the form of perforation 27 may also be provided.

Figure 2:
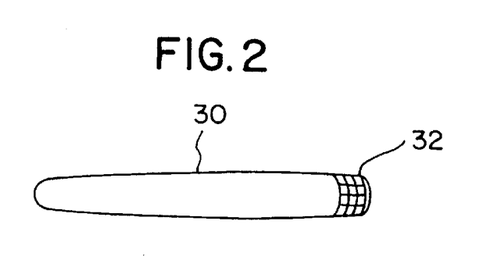
FIG. 2 is a pictorial view of an inserter that may be used to insert the towelette into the vagina.

An inserter 30 (FIG. 2) may be optionally used to assist in inserting towelette 20 and string 28 into the vagina. In its illustrated form, inserter 30 is a smooth, blunt-ended device approximately 5 to 8 inches in length. Inserter 30 may include a hook 32 on one end to facilitate removal of the towelette. Depending on a woman's preference, she may insert the towelette using her finger or an inserter.

Towelette 20 may be folded and individually packaged in small moisture-proof packets 34 (FIG. 3) similar in size and composition to packets containing conventional cleaning wipes or condoms.

The preventive formulation of the device may consist of nonoxynol-9 gel, or may be made of any agent, new or existing, appropriate for such use. Potential agents which may be used with this invention include, but are not limited to: hydrogen peroxide, carbamide peroxide, benzalkonium chloride, various types of monoclonal antibodies, C-31G (a formulation being developed by BioSyn, Inc.), cholates and desoxycholates, Buffer-Gel (a formulation being developed by ReProtect, Inc.), chlorhexidine, and sulfated or sulfonated polymers of various types (e.g. dextran and carrageenan).

The towelette of the invention may be inserted into the vagina either immediately before, or up to several hours before intercourse, and protects the user from pregnancy or from certain sexually transmitted diseases, or both.

During intercourse, the penis will rub and push against the towelette. In some cases, the motion of the penis will compress the towelette into a crumpled disc in the upper vagina to give a physical barrier.

With respect to the prevention of sexually transmitted diseases, the preventive formulation disposed on the towelette may be spread over the anatomical surface of the vagina during insertion of the towelette to provide temporary but effective protection against certain STDs.

The volume of the preventive formulation delivered to the vagina by the towelette may be on the order of about 1 ml to about 10 ml, preferably 5 ml or less.

Figure 5:
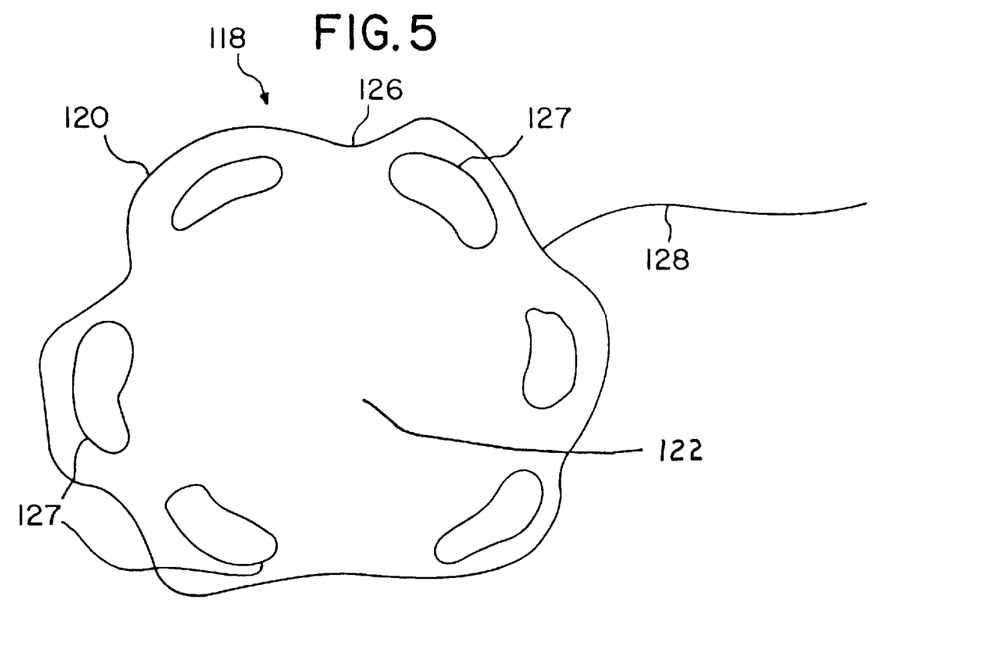
FIG. 5 is a top view of a second vaginal device of the invention.

Referring now to the embodiment of FIG. 5, device 118 includes a towelette 120 that is formed of sheet material similar to that of towelette 20 of FIG. 1. Towelette 120 is moistened with a preventive formulation in the form of a flowable spermicidal and/or microbicidal composition which may be a liquid, cream or gel, in the same fashion as towelette 20, with or without the optional reservoir.

Towelette 120 includes a central portion 122 without perforations, and has a scalloped outer rim 126 with multiple perforations 127 so that it resembles a lace doily. The towelette may be colored to further improve aesthetic appeal. In addition to the aesthetic feature provided by perforations 127, the perforations have a functional purpose in that the towelette may be removed from the vagina by a finger engaging and catching a perforation. Additionally, towelette 120 may be provided with a removal means in the form of a string 128.

The description will now turn to a discussion of several additional embodiments of the invention that include a rigid or semi-rigid support structure that is inserted into the vagina along with the towelette. More specifically, each of the embodiments illustrated in FIGS. 6–12 includes a support structure in the form of a ring that is used to assist in removal of the towelette following intercourse. The ring also serves to assist in locating and maintaining the shape of the towelette during intercourse. In all embodiments illustrated in FIGS. 6–12, the ring is formed of a soft flexible material. The softness of the material, as measured by a durometer, preferably will not be less than about Shore A 35 or greater than about Shore A 70. Tear strength values of the preferred ring materials are in the range of 5 to 10 lbs., as measured by a pull test. Preferred materials are able to withstand an 8 to 10 lb. pull before failure.

Biocompatibility of the ring material is based on blood/material interaction data, animal implant testing, and cytotoxicity testing. Preferred materials are biocompatible and elastomeric at body temperature. Also, preferred materials lack the addition of chemicals that lead toward leachable material, and the materials preferably are chemically resistant so that they do not degrade when exposed to low concentrations of various solvents.

The preferred ring materials are typified by silicone elastomer, diisocyanates (exemplified by polyurethane elastomer or silastic polyurethane), or styrene-butadiene block co-polymers (for example GLS Kraton). The types of processing for forming the ring may include liquid injection molding, liquid castable, or pellet injection molding. Other materials may be used if formulated to high standards. These materials include, but are not limited to, acrylate-butadiene, bromoisobutene-isoprene, butadiene, chlorinated polyethylene, chloroisobutene-isoprene, chloropene, chlorosulfonated polyethylene, chlorotrifluoroethylene-vinyllidene fluoride, epichlorohydrin (homo-and co-polymer), ethylenepropylene copolymer, terpolymer, fluorosilicone, isobuteneisoprene, isoprene, nitrile-butadiene, nitrile-chloroprene, nitrile-isoprene, polyacrylate, pyridine-butadiene, pyridinestyrene-butadiene, styrene-chloroprene, and styrene-isoprene.

The ring is appropriately sized to achieve the desired function, with a ring size having an outside diameter of approximately 50–70 mm and a cross sectional diameter of approximately 5–10 mm being preferred. The ring may be disposable with the towelette after intercourse, in which case the ring is preferably permanently affixed to the towelette, or the ring may be reusable, in which case the ring may fit into a pocket in the towelette or otherwise be separable from the towelette after intercourse.

It will be appreciated that the mentioned ring is one preferred form of a rigid or semi-rigid support structure to be used in conjunction with the towelette. Other forms for the support structure, such as a ball, disc or a multifaceted cube, may be used.

Figure 6:
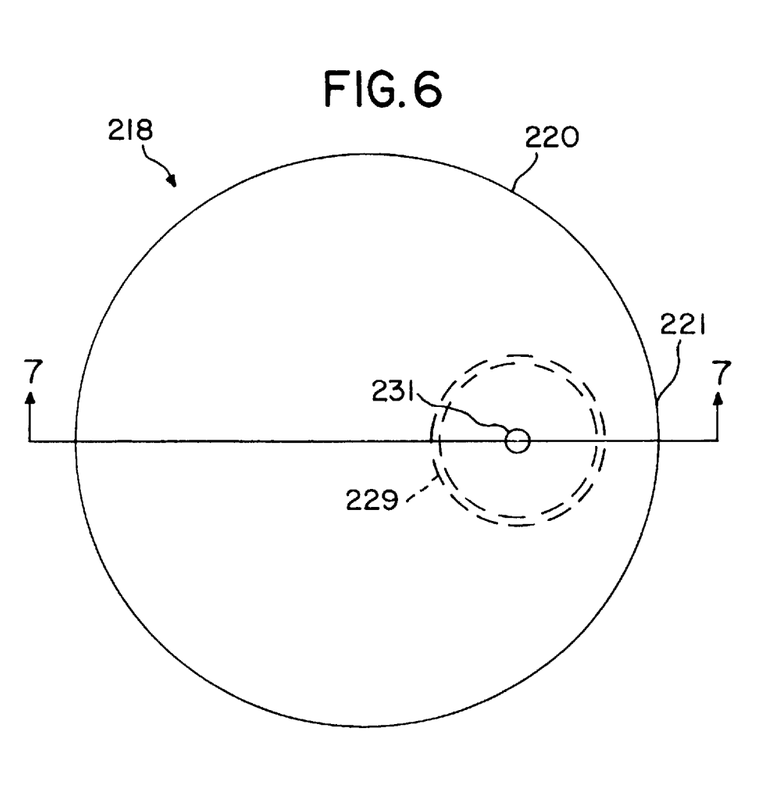
FIG. 6 is a top view of a third vaginal device of the invention incorporating a folded towelette and an affixed support structure in the form of a ring.
Figure 7:
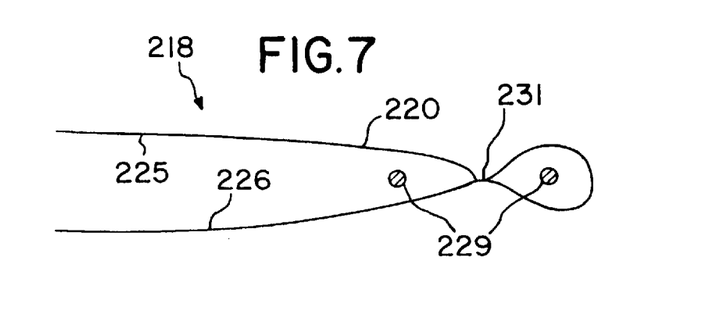
FIG. 7 is a sectional view of the towelette of FIG. 6 taken along the line 7—7.

Referring to FIGS. 6 and 7, device 218 includes a towelette 220 formed of absorbent fibrous material as described above. Towelette 220 is folded at fold line 221 to create opposing towelette faces 225, 226. A ring 229 as described above is placed between opposed faces 225, 226 and the faces are spot bonded together within the ring at 231 to affix the ring to the towelette. The spot bonding may be achieved by heat sealing, adhesives, or other suitable means. The ring support structure is used to facilitate insertion of the towelette, to facilitate appropriate positioning of the towelette so that it may serve as a physical barrier during intercourse, and to facilitate removal of the towelette after intercourse. It is contemplated that the ring in this embodiment be disposable along with the towelette.

While towelette 220 of FIGS. 6 and 7 is formed from a single sheet of material with a fold line, two opposed sheets may be used, with the two sheets being joined together into a unitary towelette by the spot bond.

Figure 8:
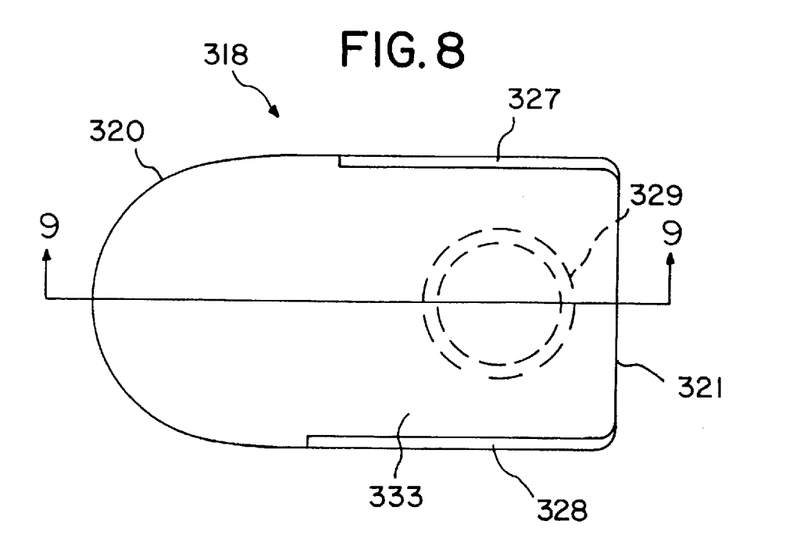
FIG. 8 is a top view of a fourth vaginal device of the invention that includes a towelette having a pocket that holds a support structure in the form of a reusable ring.
Figure 9:
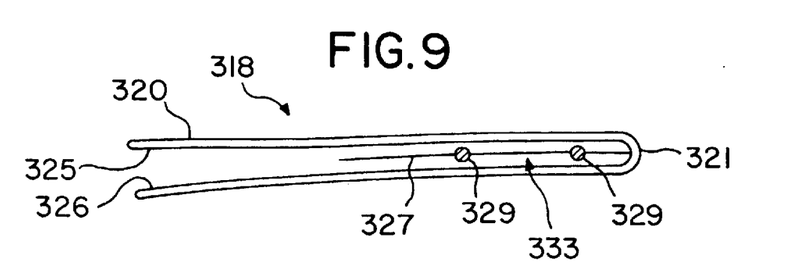
FIG. 9 is a sectional view of the towelette of FIG. 8 taken along the line 9—9.

FIGS. 8 and 9 illustrate another device 318 of the invention wherein the sheet material of towelette 320 is folded upon itself along a fold line 321 to create opposed towelette faces 325, 326. The edges of the towelette at 327, 328 are then joined or sealed by suitable means, for example, an adhesive, thermal bonding or stitching, to form a pocket 333 bounded by fold line 321 and sealed edges 327, 328. Prior to insertion of towelette 320 into the vagina, a ring 329 as described above is inserted into pocket 333. In this embodiment the ring serves the same functions as described above in connection with the previous embodiment. After intercourse, the ring and towelette are removed together. Because the ring is separable from the towelette, it may be reused after washing.

Figure 3:
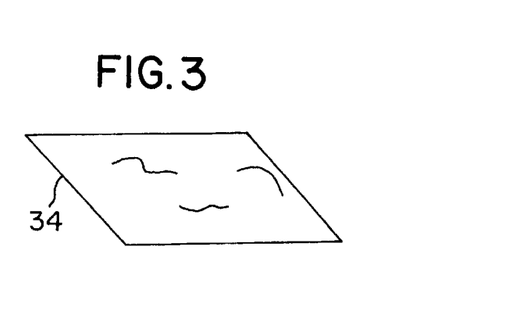
FIG. 3 is a pictorial view of a package, similar to a conventional package for condoms or cleaning wipes, for packaging the device of FIG. 1.

The towelette of the embodiment of FIGS. 8 and 9 may be packaged by itself in folded fashion in a package as shown in FIG. 3. The towelette is simply removed from the package, unfolded to expose the opening to pocket 333, and the ring is inserted into the pocket. The towelette and ring are then inserted into the vagina before intercourse. After intercourse, the towelette and ring are removed by simply grasping the ring.

Figure 10:
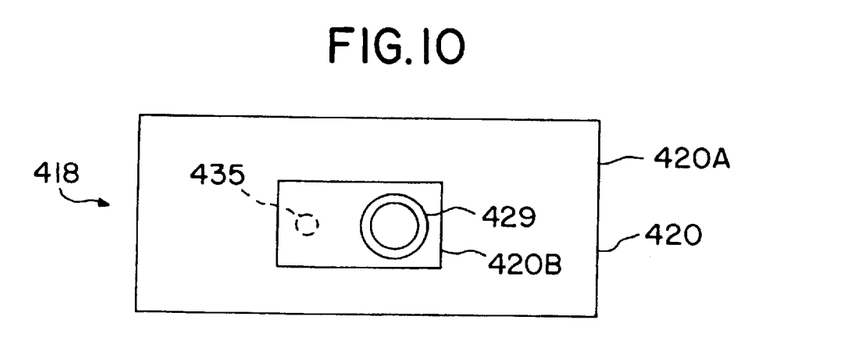
FIG. 10 is a top view of a fifth vaginal device of the invention.

FIG. 10 illustrates another device 418 of the invention including a towelette 420. Towelette 420 includes a first large sheet 420A that is spot bonded at 435 to a second smaller sheet 420B. A ring 429 is fixedly secured to the smaller sheet by adhesive or other suitable means. This embodiment is used in the same fashion as the embodiment of FIGS. 6 and 7 with the ring preferably being discarded along with the towelette after use.

Figure 11:
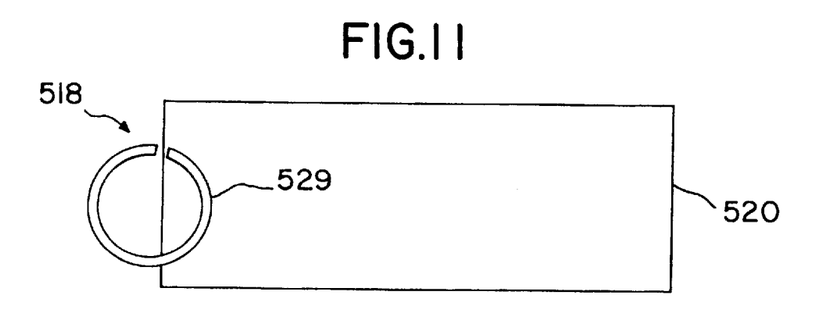
FIG. 11 is a top view of a sixth vaginal device of the invention including a reusable snap-on ring that is removably attached to the towelette.
Figure 12:
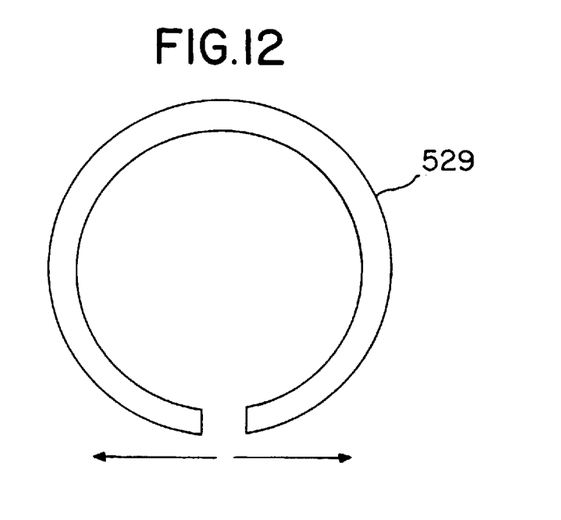
FIG. 12 is an enlarged view of the snap-on ring of FIG. 11.

FIG. 11 illustrates yet another device 518 wherein the towelette 520 is a single sheet and the ring takes the form of a reusable snap-on ring 529. As shown in FIG. 12, ring 529 may be opened by application of outwardly directed force in the direction of the arrows so that the towelette may be placed therebetween and then secured to the ring when the force is released.

Figure 13:
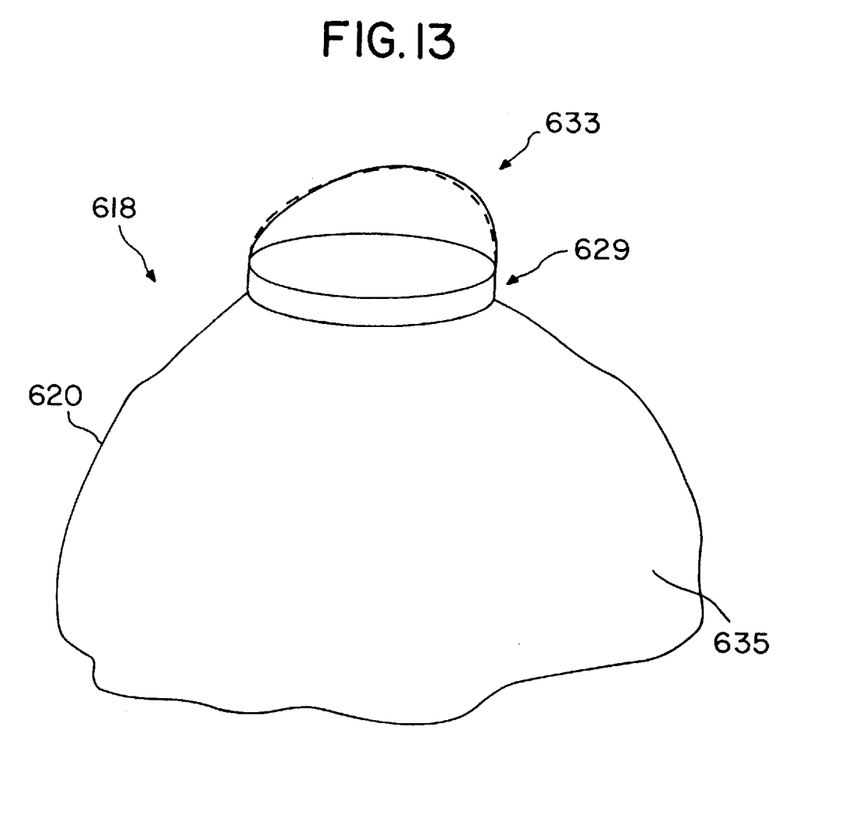

FIG. 13 illustrates another device 618 having a towelette 620 joined to a flexible ring 629 to form a unitary structure defining a dome 633 and a depending skirt 635. The material for the towelette may be as described above in connection with other embodiments. Alternatively, the ring 629 and towelette 620 may be formed as a single unit of absorbent material, for example, a suitable polymer material such as polyurethane foam or polyvinylalcohol foam. A preferred way to form ring 629 and towelette 620 of this material is by liquid injection molding. The pore size, density, percent of open cells, and the chemical properties of the material can be controlled and varied, by those skilled in the art, to meet design goals, including the ability to carry the desired amount of active agent.

While the invention has been described in connection with certain illustrated embodiments, it will be appreciated that modifications may be made without departing from the true spirit and scope of the invention.

That which is claimed is:

1. A vaginal device comprising:
   a towelette formed of absorbent sheet material sized to fit within the vagina of a human female while permitting intercourse to take place; and an effective amount of a flowable preventive formulation incorporated into said towelette by absorption.

2. A method for providing protection against pregnancy or sexually transmitted disease, or both, comprising inserting a vaginal device according to claim 1 into the vagina of a human female prior to intercourse and permitting the towelette of the device to become compressed into a crumpled disc shape in the upper vagina during the intercourse where the towelette effectively functions in both physical and chemical barrier.

3. A vaginal device according to claim 1 including means hand engagable by the female user of the device for facilitating removal of said towelette after use.

4. A vaginal device according to claim 3 wherein said means for facilitating removal comprises a hand-engagable structure at the peripheral edges of said towelette.

5. A vaginal device according to claim 4 wherein said structure at the peripheral edge of said towelette comprises perforations in the towelette sheet material.

6. A vaginal device according to claim 3 wherein said means for facilitating removal comprises a string.

7. A vaginal device according to claim 3 wherein said means for facilitating removal comprises a rigid or semi-rigid support structure that is inserted into the vagina with the towelette and removed with the towelette following intercourse.

8. A vaginal device according to claim 7 wherein said support structure comprises a ring.

9. A vaginal device according to claim 8 wherein said ring is secured to the towelette.

10. A vaginal device according to claim 9 wherein said ring is secured between opposed faces of the towelette sheet material.

11. A vaginal device according to claim 8 wherein said ring is not fixedly secured to said towelette, but is adapted to become intimately entangled with the towelette during intercourse.

12. A vaginal device according to claim 11 wherein said towelette includes a pocket for receiving said ring.

13. A vaginal device according to claim 1 wherein said preventive formuation is selected from the group consisting of nonoxynol-9, hydrogen peroxide, carbamide peroxide, benzalkonium chloride, monoclonal antibodies, C-31G, Buffer-Gel, chlorhexidine, and sulfated or sulfonated polymers.

14. A vaginal device according to claim 1 wherein said towelette includes a reservoir permitting the towelette to hold an amount of preventive formulation greater than that amount which may be held solely by absorption into the towelette sheet material.

15. A vaginal device according to claim 1 wherein said towelette sheet material is a nonwoven fabric on which instructions for use of the device are printed.

16. A vaginal device according to claim 15 wherein said nonwoven fabric includes polyester.

17. A vaginal device according to claim 16 wherein said nonwoven fabric comprises a polyester/cotton blend.

18. A vaginal device according to claim 1 wherein said towelette has an area between about 9 to about 36 square inches.

19. A vaginal device according to claim 1 made of unitary construction, where both the ring and the sheet material are made of a single polymer material.

20. A vaginal device according to claim 19 wherein said polymer material is selected from the group consisting of polyurethane foam and polyvinylalcohol foam.

* * * * *

UNITED STATES PATENT AND TRADEMARK OFFICE
CERTIFICATE OF CORRECTION

PATENT NO. : 5,819,742
DATED : October 13, 1998
INVENTOR(S) : David C. Sokal, et al.

It is certified that error appears in the above-indentified patent and that said Letters Patent is hereby corrected as shown below:

At column 1, line 5 insert:

-- GOVERNMENT LICENSE RIGHTS

The invention claimed herein was made under U.S. Agency for International Development Contract No. CCP-A-OO-95-00022-02, and the U.S. government has certain rights therein. --

Signed and Sealed this

Twenty-third Day of March, 1999

Attest:

Q. TODD DICKINSON

Attesting Officer

Acting Commissioner of Patents and Trademarks